United States Patent [19]

Nishimura et al.

[11] 4,435,569

[45] Mar. 6, 1984

[54] 5-[SUBSTITUTED AMINO METHYL]PYRROLO[2,3-D]PYRIMIDINE-4-ONE

[75] Inventors: Susumu Nishimura, Ichihara; Hiroaki Nomura, Takstsuki, both of Japan

[73] Assignee: Takeda Chemical Industries, Ltd., Osaka, Japan

[21] Appl. No.: 423,243

[22] Filed: Sep. 24, 1982

[30] Foreign Application Priority Data

Nov. 18, 1981 [JP] Japan .................................. 56-184653

[51] Int. Cl.³ .................. C07D 487/04; A61K 31/505
[52] U.S. Cl. ..................................... 544/280; 424/251
[58] Field of Search ......................................... 544/280

[56] References Cited

U.S. PATENT DOCUMENTS 3,598,824 8/1971 Troxler et al. ...................... 544/280
3,657,245 4/1972 Bormann et al. ................... 544/280
4,229,453 10/1980 Roth et al. ............................ 424/251

FOREIGN PATENT DOCUMENTS 312366 5/1959 United Kingdom ................ 544/280

OTHER PUBLICATIONS

S. Nishimura et al., GANN Monograph on Cancer Research, 24, 245–262, (1979).

J. R. Katze et al., Biochem. Biophys. Res. Comm., 96, 313–319, (1980).

Primary Examiner—Donald G. Daus
Assistant Examiner—S. A. Gibson
Attorney, Agent, or Firm—Wegner & Bretschneider

[57] ABSTRACT

Novel deazapurine derivatives of the formula:

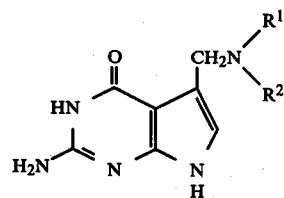

wherein $R^1$ is $C_{1-18}$ alkyl which may be substituted with di-$C_{1-3}$ alkyl amino; $C_{1-18}$ alkenyl; $C_{3-8}$ cyloalkyl; $C_{5-8}$ cycloalkenyl; $C_{7-13}$ aralkyl which may be substituted with $C_{1-4}$ alkoxy, $C_{1-4}$ alkanoyl, $C_{2-4}$ alkoxycarbonyl, hydroxy, amino, nitro, trifluoromethyl or $C_{1-4}$ alkanoylamido; or $C_{6-10}$ aryl and $R^2$ is hydrogen or $C_{7-13}$ aralkyl or, $R^1$ and $R^2$, taken together with the adjacent nitrogen atom, form a piperidine ring, and salt thereof are selectively taken up by tumor cells and have antitumor activity.

10 Claims, No Drawings

5-[SUBSTITUTED AMINO METHYL]PYRROLO[2,3-D]PYRIMIDINE-4-ONE

This invention relates to novel 7-deazapurine derivatives which are of value as antitumor agents.

Naturally modified bases having the same nucleus as compounds of this invention (for example, Q base, PreQ$_1$ base, Pre Q$_0$ base) occur broadly as components of tRNA (tRNA$^{Tyr}$, tRNA$^{His}$, tRNA$^{Asp}$ and tRNA$^{Asn}$) in animals, plants and microorganisms and it has been recognized that these bases are situated as the first position of the anticodon of the respective tRNAs mentioned above. Therefore, it has been considered that Q bases are exerting direct and important biological influences upon the recognition of genetic information from mRNAs and the function of tRNA to convert such information to amino acid sequences of proteins.

On the other hand, recent advances in fundamental research on malignancy have led to a rapidly expending knowledge of the structure of tRNA and the role thereof in vital phenomena. One of the most important findings is the basic elucidation of the above-mentioned Q bases. Thus, it has been discovered that unlike normal cells, tumor cells contain Q base-deficient tRNA and that the existence of Q base-deficient tRNA is a phenomenon observed in tumor cells in common. Moreover, the existence of tRNA-guanine transglycosidase has been established in tumor cells as well as in normal cells and it has been elucidated that when Q bases are given exogenously, Q base-deficient tRNAs take up the Q base into designated positions and thereby return to normal tRNAs [Akira Nishimura et al., GANN Monograph on Cancer Research, 24, 245–262 (1979)].

The present inventors synthesized a variety of Q base derivatives and investigated their effects on malignant tissues. As a result, they discovered some compounds which display excellent antitumor activity through a new mode of action. The present invention has been accomplished on the basis of the above new finding.

Thus, this invention relates to 7-deazapurine derivatives having the formula:

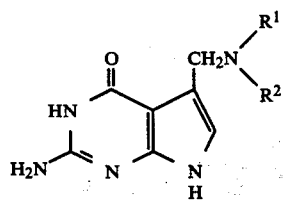

(I)

wherein $R^1$ is $C_{1-18}$ alkyl which may be substituted with di-$C_{1-3}$ alkylamino; $C_{1-18}$ alkenyl; $C_{3-8}$ cycloalkyl; $C_{5-8}$ cycloalkenyl; $C_{7-13}$ aralkyl which may be substituted with $C_{1-4}$ alkoxy, $C_{1-4}$ alkanoyl, $C_{2-4}$ alkoxycarbonyl, hydroxy, amino, nitro, trifluoromethyl or $C_{1-4}$ alkanoylamido; or $C_{6-10}$ aryl and $R^2$ is hydrogen or $C_{7-13}$ aralkyl or, $R^1$ and $R^2$, taken together with adjacent nitrogen atom, form a piperidine ring, and salts thereof.

Referring to $R_1$ in the above formula (I), the $C_{1-18}$ alkyl may be, for example, methyl, ethyl, propyl, isopropyl, butyl, isobutyl, sec-butyl, tert-butyl, pentyl, isopentyl, hexyl, isohexyl, heptyl, octyl, nonyl, decyl, undecyl, dodecyl, tetradecyl, hexadecyl, octadecyl, 1,2-dimethylpropyl, 1-ethylpropyl, 1,2,2-trimethylpropyl, 1-propylbutyl or 2-ethylhexyl, and among others, $C_{1-6}$ alkyl is preferred. These alkyls may be substituted with di-$C_{1-3}$ alkylamino, such as dimethylamino, diethylamino, dipropylamino. $C_{1-18}$ alkenyl may be, for example, vinyl, allyl, 1-methylvinyl, 2-methylvinyl, 1-octenyl or 1-decenyl and among others, $C_{1-6}$ alkenyl is preferred. $C_{3-8}$ cycloalkyl may be, for example, cyclopropyl, cyclobutyl, cyclopentyl, cyclohexyl, cycloheptyl or cyclooctyl, and $C_{4-6}$ cycloalkyl is preferred. $C_{5-8}$ cycloalkenyl may be, for example, cyclopentenyl, cyclohexenyl, cycloheptenyl, cyclooctenyl, cyclopentadienyl, cyclohexadienyl, cycloheptadienyl or cyclooctadienyl. $C_{7-13}$ aralkyl may be, for example, benzyl, α-methylbenzyl, phenethyl or diphenylmethyl and among them, benzyl is preferred. $C_{6-10}$ aryl may be, for example, phenyl, α-naphthyl or β-naphthyl, and among them phenyl is preferred.

Referring to $R^2$ in the formula (I), $C_{7-13}$ aralkyl may be, for example, the same as $C_{7-13}$ aralkyl mentioned in $R^1$.

$C_{7-13}$ aralkyl as $R^1$ may be substituted. Examples of such substituents include alkoxy groups of about 1 to 4 carbon atoms (e.g. methoxy, ethoxy, propoxy, isopropoxy, n-butoxy, iso-butoxy, sec-butoxy, tert-butoxy), alkanoyl groups of about 1 to 4 carbon atoms (e.g. formyl, acetyl, propionyl, n-butyryl, iso-butyryl), alkoxycarbonyl groups of about 2 to 4 carbon atoms (e.g. methoxycarbonyl, ethoxycarbonyl, n-propoxycarbonyl, iso-propoxycarbonyl), hydroxy, amino, nitro, trifluoromethyl, alkanoylamido (e.g. formamido, acetamido, propionamido, butyramido, iso-butyramido) and $C_{1-4}$ is preferred. The $C_{7-13}$ aralkyl not substituted with halogen is preferred.

Salts of compound (I) may be pharmaceutically acceptable salts, such as salts with mineral acid (e.g. hydrochloric acid, sulfuric acid, phosphoric acid, boric acid) and salts with organic acid (e.g. oxalic acid, tartaric acid, acetic acid, benzenesulfonic acid, p-toluenesulfonic acid, camphorsulfonic acid, etc.).

The compound (I) of this invention can be produced, for example, by the processes shown below.

(A) A compound of the formula:

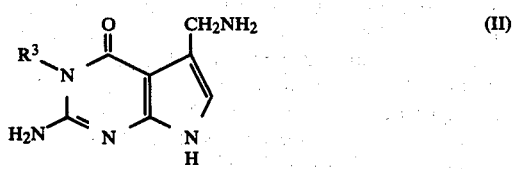

(II)

wherein $R^3$ is hydrogen or isopropyloxymethyl, is condensed with an aldehyde or ketone of the formula:

(III)

wherein $R^1$ and $R^2$ are the same as defined above, to give a Schiff's base of the formula:

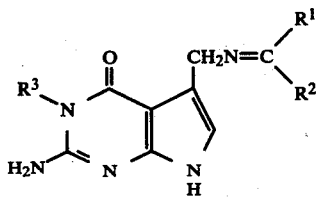

wherein $R^1$, $R^2$ and $R^3$ are respectively as defined above, and this Schiff's base is then reduced. Or, (II) and (III) are condensed under reducing conditions. Then, where $R^3$ is

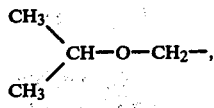

the reaction product is further deprotected. By either of the above procedure can be produced a 7-deazapurine derivative of the formula (I).

This reaction is conducted using compounds (II) and (III) in the molar ratio (III/II) of about 3 to 0.5, either in the absence of a solvent or in the presence of a suitable solvent. It is conducted at a temperature between $-10°$ C. and the boiling point of the reaction solvent, preferably within the range of 0° to 50° C., for 10 min. to 48 hours. This reaction gives a compound (IV). In conducting this reaction, it is possible to employ (III) whose aldehyde or ketone group has been protected in the form of an acetal or ketal. The reaction solvent is preferably a non-aqueous solvent, such as methanol, ethanol, n-propyl alcohol, iso-propyl alcohol, ether, tetrahydrofuran, dioxane, acetonitrile, methyl acetate, ethyl acetate, dichloromethane, chloroform, carbon tetrachloride, dichloroethane, acetone, dimethyl sulfoxide, dimethylformamide, benzene, toluene, xylene, etc. To improve the reaction rate and yield, there may be added a dehydrating agent such as molecular sieve, calcium chloride, magnesium sulfate, sodium sulfate, calcium sulfate, etc. The product compound (IV) can be isolated from the reaction system by conventional purification/separation procedures such as concentration, extraction with a solvent, recrystallization, chromatography, etc. The reaction mixture may, without isolation of (IV), be directly submitted to the next reducing reaction.

The reducing reaction is conducted by catalytic reduction or by means of a hydride in a suitable solvent at a temperature from about $-40°$ C. to the boiling point of the solvent, preferably at about 0° to 50° C. The solvent may for example be water, methanol, ethanol, n-propyl alcohol, isopropyl alcohol, ether, tetrahydrofuran, dioxane, methyl acetate, ethyl acetate, benzene, toluene, xylene or the like or a mixture thereof. The catalyst for use in catalytic reduction may for example be palladium, platinum, rhodium or the like. In addition, acetic acid, hydrochloric acid, sulfuric acid or the like may be added in a small proportion. When the reduction reaction is conducted with a hydride, the hydride may for example be lithium aluminum hydride, sodium borohydride, lithium borohydride, sodium cyanoborohydride, or the like. The amount of such reducing agent, relative to the Schiff's base, is about 1 to 100 molar equivalents and usually about 2 to 20 equivalents. Where $R^3$ is

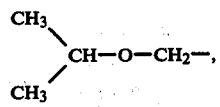

the protective group can be easily removed by reacting the reduction product with dilute hydrochloric acid, dilute sulfuric acid, aqueous trifluoroacetic acid or the like at a temperature of 30 to 100° C. for 30 min. to 2 days.

The starting compound (II) used in the above-described process can be easily produced by the known method described in the literature [N. Okada et al; J. Biol. Chem. 254, 3067 (1979)]. The mating starting compound (III) may be a known compound or a compound prepared by a known process for the known compound.

(B) A compound of the formula:

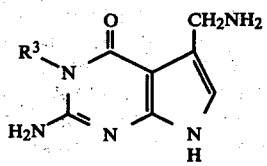

wherein $R^3$ is as defined above, is reacted with an alkylating agent of the formula:

wherein $R^1$ is as defined above and X is halogen (chlorine, bromine, iodine etc.), benzenesulfonyl, p-toluenesulfonyl or methanesulfonyl, and, if there exists a protective group, the condensation product is deprotected with an acid to give a 7-deazapurine derivative of the formula:

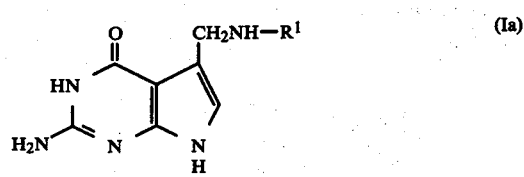

wherein $R^1$ is as defined above.

In this reaction, compounds (II) and (V) are reacted in the molar ratio (V)/(II) of about 0.5 to 2.0 in a suitable reaction solvent at a temperature between $-10°$ C. and the boiling point of the solvent, preferably between 0° C. and 100° C., for 10 min. to 7 days, whereby the compound (Ia) can be obtained. Examples of the reaction solvent include water, methanol, ethanol, n-propyl alcohol, iso-propyl alcohol, ether, tetrahydrofuran, dioxane, methyl acetate, ethyl acetate, benzene, toluene, xylene, dimethyl sulfoxide, dimethylformamide, and acetonitrile as well as mixtures of such solvents. The reaction rate and yield can be improved by using an acid acceptor such as sodium hydrogen carbonate, sodium carbonate, potassium carbonate, calcium carbonate, silver carbonate, sodium hydroxide, potassium hydroxide, lithium hydroxide, calcium hydroxide, barium hydroxide, magnesium oxide, triethylamine, pyridine, N,N-dimethylaniline, etc. Where the protective group

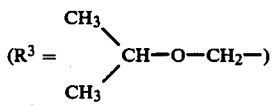

is present, it can be easily removed by means of an acid under the same conditions as described for Process A.

The starting compound (V) to be used in this process may also be a known compound or a compound prepared by the procedure known for the production of such known compound.

(C) A compound of the formula:

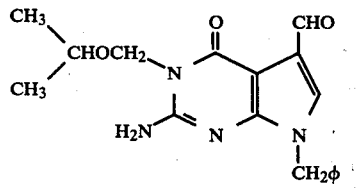

is condensed with an amine of the formula:

$$H_2N-R^1 \quad (VII)$$

wherein $R^1$ is as defined above, to give a Schiff's base of the formula:

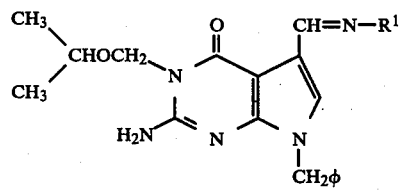

wherein $R^1$ is as defined above, and this Schiff's base is reduced as described in (A) to give a compound of the formula:

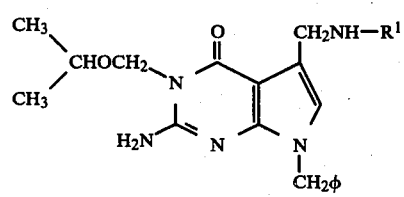

wherein $R^1$ is as defined above. Thereafter, the compound (IX) is debenzylated in the conventional manner (e.g. with liquid ammonia-lithium metal, lithium ammonia-sodium metal). Then, in the same manner as in Processes A and B, the

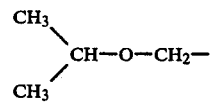

group is deprotected to give a compound (Ia). The starting compound (VI) can also be easily prepared by the known process described in the literature [N. Okada et al, J. Biol. Chem. 254, 3067 (1979)]. The other starting compound (VII) may be a known compound or a compound prepared by a procedure known for the production thereof.

(D) The processes of A, B and C may be followed in a suitable combination to give a desired new 7-deazapurine derivative of the formula:

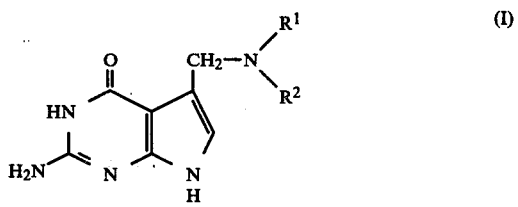

wherein $R^1$ and $R^2$ are as defined above.

The compound (I) of this invention as produced by any of the above processes can be isolated from the reaction mixture by the conventional purification procedure such as concentration, extraction with a solvent, chromatography, recrystallization, etc. The compound (I) may be converted to the aforementioned salt and, then, isolated from the reaction mixture.

The 7-deazapurine derivative (I) and said pharmaceutically acceptable salt thereof are selectively taken up by tumor cells to display an excellent antitumor activity in warm-blooded animals and especially in mammals. This property plus its extremely low toxicity makes the derivative (I) and a salt thereof useful medicines. For example, growth of Sarcoma 180, Ehrlich carcinoma, etc. as transplanted into the mouse can be inhibited by the intravenous, subcutaneous or oral administration of compound (I) or salt in a single-dose or repeated-dose schedule. The compound (I) or salt thereof can be administered either as it is or as formulation with pharmaceutically acceptable carriers, vehicles, diluents or the like into such dosage forms as powders, granules, tablets, capsules, suppositories, injections, etc. While the dosage depends on the subject animal species, disease, condition, the particular species of compound, route of administration, etc., the daily dose can be selected from the range of about 0.05 to 100 mg/kg body weight, preferably 0.1 to 10 mg/kg body weight.

Since the compound (I) and a salt thereof are inhibitory against various microorganisms, it is of value as a drug for the treatment of bacterial infections in warm-blooded animals and especially in mammalian animals. When the derivative (I) or salt thereof is used as a fungicide or disinfectant, it can be used as dissolved in water, an isotonic salt solution, an isotonic glucose solution, Ringer's solution, etc. at a concentration of 1 to 1000 mg/ml or as dispersed in a non-aqueous liquid such as a vegetable (cottonseed, peanut, corn, sesame) oil at the same concentration or as tablets formulated with 1 to 1000 mg of an excipient such as lactose, starch, talc or the like.

EXPERIMENTAL EXAMPLE 1

One$\times 10^6$ Sarcoma 180 cells were subcutaneously transplanted into the right groin of an ICR mouse weighing about 20 grams and starting 24 hours after transplantation, 0.5 mg/kg of the compound of Example 1 in distilled water for injection was intraperitoneally administered once daily for 20 consecutive days. On day 35 after transplantation, the tumorous node was incised, weighed and compared with the specimen of the control (without medication) group. The percent inhibition was 58% relative to the control.

EXPERIMENTAL EXAMPLE 2

The experiment described in Experimental Example 1 was repeated except that mice transplanted with Ehlrich carcinoma cells were employed. The percent inhibition rate was 75%.

EXPERIMENTAL EXAMPLE 3

Inhibitory effect upon the multiplication of tumor cells

The inhibitory effects of compound (I) upon the multiplication of cells were detected using L5178Y cells (tumor cell) in RPMI1640 medium+10% fetal calf serum for 48 hours at 37° C.

The result was expressed in the concentration of the drug giving a cell count of 50% ($ED_{50}$) with the average number of cells for the control (not medicated) group on the 2nd day being taken as 100%.

| Compound (Example No.) | $ED_{50}$ (μg/ml) |
| --- | --- |
| 2-Amino-5-cyclopentylaminoethylpyrro-[2,3-d]pyrimidin-4-one (2) | 40 |
| 2-Amino-5-piperidinomethylpyrrolo-[2,3-d]pirimidin-4-one (3) | 120 |
| 2-Amino-5-benzylaminomethylpyrrolo-[2,3-d]pyrimidin-4-one (4) | 30 |
| Q base | >200 |

EXAMPLE 1

Production of
2-amino-5-propylaminomethylpyrrolo[2,3-d]pyrimidin-4-one (dihydrochloride)

In 5.0 ml of dry methanol were dissolved 251 mg of 2-amino-5-aminomethyl-3-isopropyloxymethylpyrrolo[2,3-d]pyrimidin-4-one and 64 mg of propionaldehyde and the solution was allowed to stand under stirring at room temperature for 30 min. Then, 20 mg of sodium borohydride was added and the mixture was reacted at room temperature for an hour. The excess reagent was decomposed with a small amount of acetic acid, the solvent was distilled off under reduced pressure and the residue was purified by silica gel column chromatography to give 76 mg of 2-amino-5-propylaminomethyl-3-isopropyloxymethylpyrrolo[2,3-d]pyrimidin-4-one. The whole amount of this product was dissolved in 30 ml of 2 N—HCl and, after nitrogen purging, hydrolyzed under heating at 70° C. for 6.5 hours. The solvent was then evaporated off under reduced pressure to give 73 mg of the desired compound.

NMR($D_2O$, 60 MHz) δ: 0.90(t,3H), 1.67(m,2H), 3.00(t,2H), 4.23(s,2H), 6.93(s,1H).

IR(Nujol) ν: 3175, 2720, 1675 $cm^{-1}$.

EXAMPLE 2

Production of
2-amino-5-cyclopentylaminomethylpyrrolo[2,3-d]pyrimidin-4-one (dihydrochloride)

In 10 ml of dry methanol were dissolved 251 mg of 2-amino-5-aminomethyl-3-isopropyloxymethylpyrrolo[2,3-d]pyrimidin-4-one and 252 mg of cyclopentanone and the mixture was allowed to stand under stirring at room temperature for 30 min. The mixture was then cooled to 0° C. and treated with 38 mg of sodium borohydride for 2 hrs. The excess reagent was decomposed with acetic acid, the solvent was distilled off under reduced pressure and the residue was purified by silica gel column chromatography to give 218 mg of 2-amino-5-cyclopentylaminomethyl-3-isopropyloxymethylpyrrolo[2,3-d]pyrimidin-4-one. The whole amount of this product was dissolved in 60 ml of 2 N—HCl and, after nitrogen purging, hydrolyzed at 70° C. for 5 hrs. The solvent was then evaporated to dryness under reduced pressure to give 196 mg of the desired compound.

NMR($D_2O$/$CD_3OD$, 60 MHz) δ: 1.67–2.40(m,8H), 3.67(m,1H), 4.30(s,2H), 7.00(s,1H).

IR(KBr) ν: 3200, 3100–2400, 1680, 1600 $cm^{-1}$.

EXAMPLE 3

Production of
2-amino-5-piperidinomethylpyrrolo[2,3-d]pyrimidin-4-one (dihydrochloride)

In 4.5 ml of methanol were dissolved 151 mg of 2-amino-5-aminomethylpyrrolo[2,3-d]pyrimidin-4-one (dihydrochloride) and 138 mg of 1,5-dibromopentane, followed by addition of 2.4 ml of 1 N-sodium hydroxide. The mixture was stirred at room temperature for 4 days. The solvent was then distilled off under pressure and the residue was purified by silica gel column chromatography. The fractions containing the desired compound were pooled and after addition of an excess of hydrogen chloride/ethanol, concentrated to dryness, followed by precipitation with ether to give 45 mg of the desired compound.

NMR($CD_3OD$/$D_2O$, 60 MHz) δ: 1.80(m,6H), 2.80–3.67(m,4H), 4.30(q,2H), 7.02(s,1H).

IR (KBr) ν: 3370, 3175–2500, 1680 $cm^{-1}$.

EXAMPLE 4

Production of
2-amino-5-benzylaminomethylpyrrolo[2,3-d]pyrimidin-4-one

In 5 ml of methanol was dissolved 251 mg of 2-amino-5-aminomethylpyrrolo[2,3-d]pyrimidin-4-one (dihydrochloride). To this solution was added 396 mg of a 28% methanolic solution of sodium methoxide, and under stirring at room temperature, 106 mg of benzaldehyde and, then, 1 g of molecular sieve (Wako Pure Chemical Co. in Japan 3 A 1/16) were added. The mixture was stirred for 30 minutes, after which 25 mg of sodium borohydride was added. The mixture was further stirred at room temperature for 30 min., and 0.3 ml of concentrated HCl and, then, 5 ml of 5.4% ammonia-ethanol were added. The insolubles were filtered off, the filtrate was concentrated, and the residue was purified by silica gel column chromatography to give 214 mg of the desired compound.

NMR(DMSO-$d_6$, 60 MHz) δ: 4.20(bs,4H), 6.50(bs,2H), 6.83(bs,1H), 7.40(bs,5H), 8.43(bs,1H), 11.33(bs,1H).

IR(KBr) ν: 3130, 1660, 1445, 1610, 1395 $cm^{-1}$.

EXAMPLE 5

Production of
2-amino-5-dibenzylaminomethylpyrrolo[2,3-d]pyrimidin-4-one

In 30 ml of methanol was dissolved 172 mg of 2-amino-5-benzylaminomethylpyrrolo[2,3-d]pyrimidin-4-one (the compound of Example 4), followed by addition of 90 mg of anhydrous potassium carbonate, 2 mg of sodium iodide and 81 mg of benzyl chloride. The mixture was stirred on a water bath at 60° C. for 4 hrs. The solvent was then distilled off and the residue was purified by silica gel column chromatography to give 57 mg of the desired compound.

NMR(CDCl$_3$/DMSO-d$_6$, 60 MHz) δ: 3.60(bs,4H), 3.80(bs,2H), 5.77(bs,2H), 6.60(bs,1H), 7.23(m,10H), 10.17(bs,1H), 10.47(bs,1H).

IR(KBr) ν: 3490, 3355, 3120, 2925, 1665, 1625, 1595 cm$^{-1}$.

EXAMPLE 6

Production of 2-amino-5-phenylaminomethyl[2,3-d]pyrimidin-4-one (dihydrochloride)

In 10 ml of dry methanol is dissolved 340 mg of 2-amino-7-benzyl-3-isopropyloxymethylpyrrolo[2,3-d]pyrimidin-4-one-5-carbaldehyde and 93 mg of aniline and the mixture is allowed to stand under stirring at room temperature for 60 min. The mixture is then cooled to 0° C. and treated with 38 mg of sodium borohydride. The excess reagent is decomposed with HCl, the solvent is distilled off under reduced pressure, and the residue is purified by silica gel column chromatography to give 285 mg of 2-amino-7-benzyl-5-phenylaminomethyl-3-isopropyloxymethylpyrrolo[2,3-d]pyrimidin-4-one. The whole amount of the above product is dissolved in 28.5 ml of liquid ammonia-dimethoxyethane (1:1) and an excess of sodium metal shavings are added until a permanent blue color is observed for more than 5 min. To this mixture is added ammonium chloride to terminate the reaction and the whole system is allowed to stand at room temperature until the liquid ammonia is removed. The dimethoxyethane is then distilled off under reduced pressure and the residue is purified by silica gel column chromatography to give 128 mg of 2-amino-5-phenylaminomethyl-3-isopropyloxymethylpyrrolo[2,3-d]pyrimidin-4-one. This product is further dissolved in 50 ml of 2 N—HCl and after nitrogen purging, hydrolyzed by heating at 70° C. for 5 hrs. The solvent is then evaporated to dryness under reduced pressure to give 120 mg of the desired compound.

MS: m/e 297 (M$^+$: determined as monoacetate).
IR(KBr) ν: 3150-2400, 1680, 1605 cm$^{-1}$.

EXAMPLE 7

Production of 2-amino-5-allylaminomethylpyrrolo[2,3-d]pyrimidin-4-one

The procedure of Example 5 is repeated except that 252 mg of 2-amino-5-aminomethylpyrrolo[2,3-d]pyrimidin-4-one (dihydrochloride) and 121 mg of allyl bromide are employed. This procedure gives 165 mg of the above-identified compound.

MS: m/e 261 (M$^+$: determined as monoacetate).

EXAMPLE 8

Production of 2-amino-5-dodecylaminomethylpyrro[2,3-d]pyrimidin-4-one (dihydrochloride)

By the same procedure as Example 1, 85 mg of the above-identified compound is obtained from 251 mg of 2-amino-5-aminomethyl-3-isopropyloxymethylpyrrolo[2,3-d]pyrimidin-4-one and 184 mg of dodecylaldehyde.

MS: m/e 389 (M$^+$: determined as monoacetate).

EXAMPLE 9

Production of 2-amino-5-(cyclohexen-3-yl)aminomethylpyrrolo[2,3-d]pyrimidin-4-one By the same procedure as Example 5, 148 mg of the above-identified compound is synthesized from 252 mg of 2-amino-5-aminomethylpyrrolo[2,3-d]pyrimidin-4-one (dihydrochloride) and 161 mg of 3-bromocyclohexene.

MS: m/e 301 (M$^+$: determined as monoacetate).

EXAMPLE 10

Production of 2-amino-5-(p-methoxybenzyl)aminomethylpyrrolo[2,3-d]pyrimidin-4-one By the same procedure as Example 5, 162 mg of the above-identified compound is synthesized from 252 mg of 2-amino-5-aminomethylpyrrolo[2,3-d]pyrimidin-4-one (dihydrochloride) and 157 mg of p-methoxybenzyl chloride.

MS: m/e 341 (M$^+$: determined as monoacetate).

EXAMPLE 11

Production of 2-amino-5-(p-hydroxybenzyl)aminomethylpyrrolo[2,3-d]pyrimidin-4-one By the same procedure as Example 4, 190 mg of the above-identified compound is synthesized from 252 mg of 2-amino-5-aminomethylpyrrolo[2,3-d]pyrimidin-4-one (dihydrochloride) and 122 mg of p-hydroxybenzaldehyde.

MS: m/e 369 (M$^+$: determined as monoacetate).

EXAMPLE 12

Production of 2-amino-5-(p-acetamidobenzyl)aminomethylpyrrolo[2,3-d]pyrimidin-4-one By the same procedure as Example 4, 178 mg of the above-identified compound is synthesized from 252 mg of 2-amino-5-aminomethylpyrrolo[2,3-d]pyrimidin-4-one (dihydrochloride) and 163 mg of p-acetamidobenzaldehyde.

MS: m/e 368 (M$^+$: determined as monoacetate).

EXAMPLE 13

Production of 2-amino-5-(p-acetylbenzyl)aminomethylpyrrolo[2,3-d]pyrimidin-4-one By the same procedure as Example 5, 175 mg of the above-identified compound is obtained from 252 mg of 2-amino-5-aminomethylpyrrolo[2,3-d]pyrimidin-4-one (dihydrochloride) and 213 mg of p-acetylbenzyl bromide.

MS: m/e 353 (M$^+$: determined as monoacetate).

EXAMPLE 14

Production of 2-amino-5-(p-isopropoxycarbonylbenzyl)aminomethylpyrrolo[2,3-d]pyrimidin-4-one By the same procedure as Example 5, 208 mg of the above-identified compound is obtained from 252 mg of 2-amino-5-aminomethylpyrrolo[2,3-d]pyrimidin-4-one (dihydrochloride) and 213 mg of isopropyl p-chloromethylbenzoate.

MS: m/e 397 (M+: determined as monoacetate).

EXAMPLE 15

Production of
2-amino-5-(p-cyanobenzyl)aminomethylpyrrolo[2,3-d]pyrimidin-4-one

By the same procedure as Example 5, 165 mg of the above-identified compound is obtained from 252 mg of 2-amino-5-aminomethylpyrrolo[2,3-d]pyrimidin-4-one (dihydrochloride) and 196 mg of p-cyanobenzyl bromide.

MS: m/e 336 (M+: determined as monoacetate).

EXAMPLE 16

Production of
2-amino-5-(m-nitrobenzyl)aminomethylpyrrolo[2,3-d]pyrimidin-4-one

By the same procedure as Example 5, 185 mg of the above-identified compound is obtained from 252 mg of 2-amino-5-aminomethylpyrrolo[2,3-d]pyrimidin-4-one (dihydrochloride) and 216 mg of m-nitrobenzyl bromide.

MS: m/e 356 (M+: determined as monoacetate).

EXAMPLE 17

Production of
2-amino-5-(o-isobutyryloxybenzyl)aminomethylpyrrolo[2,3-d]pyrimidin-4-one By the same procedure as Example 4, 128 mg of the above-identified compound is obtained from 252 mg of 2-amino-5-aminomethylpyrrolo[2,3-d]pyrimidin-4-one (dihydrochloride) and 192 mg of o-isobutyloxybenzaldehyde.

MS: m/e 397 (M+: determined as monoacetate).

EXAMPLE 18

Production of
2-amino-5-(β-diethylamino-α-methyl)ethylaminomethylpyrrolo[2,3-d]pyrimidin-4-one By the same procedure as Example 4, 181 mg of the above-identified compound is obtained from 252 mg of 2-amino-5-aminomethylpyrrolo[2,3-d]pyrimidin-4-one (dihydrochloride) and 129 mg of diethylaminoacetone.

MS: m/e 334 (M+: determined as monoacetate).

EXAMPLE 19

Production of
2-amino-5-(p-trifluoromethylbenzyl)aminomethylpyrrolo[2,3-d]pyrimidin-4-one (dihydrochloride)

By the same procedure as Example 1, 165 mg of the above-identified compound is obtained from 251 mg of 2-amino-5-aminomethyl-3-isopropyloxymethylpyrrolo[2,3-d]pyrimidin-4-one and 174 mg of p-trifluoromethylbenzaldehyde.

MS: m/e 379 (M+, determined as monoacetate).

What is claimed is:
1. A compound of the formula:

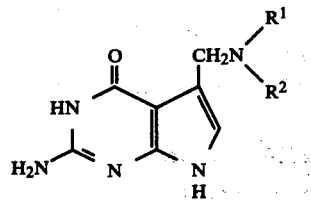

wherein
$R^1$ is $C_{1-18}$ alkyl which may be substituted with di-$C_{1-3}$ alkylamino; $C_{1-18}$ alkenyl; $C_{3-8}$ cycloalkyl; $C_{5-8}$ cycloalkenyl; $C_{7-13}$ aralkyl which may be substituted with $C_{1-4}$ alkoxy, $C_{1-4}$ alkanoyl, $C_{2-4}$ alkoxycarbonyl, hydroxy, amino, nitro, trifluoromethyl or $C_{1-4}$ alkanoylamino; or $C_{6-10}$ aryl and $R^2$ is hydrogen or $C_{7-13}$ aralkyl or, $R^1$ and $R^2$, taken together with adjacent nitrogen atom, form a piperidine ring, or a pharmaceutically acceptable salt thereof.

2. The compound according to claim 1, wherein $R^1$ is $C_{1-6}$ alkyl, $C_{4-6}$ cycloalkyl or $C_{7-9}$ aralkyl which may be substituted with $C_{1-4}$ alkoxy, $C_{1-4}$ alkanoyl, $C_{2-4}$ alkoxycarbonyl, hydroxy, amino, nitro, trifluoromethyl or $C_{1-4}$ alkanoylamido and $R^2$ hydrogen or $C_{7-9}$ aralkyl, or $R^1$ and $R^2$, taken together with the adjacent nitrogen atom, form piperidine ring.

3. The compound according to claim 1, wherein $R^1$ is $C_{1-6}$ alkyl which may be substituted with di-$C_{1-3}$ alkylamino and $R^2$ is hydrogen.

4. The compound according to claim 1, wherein $R^1$ is $C_{4-6}$ cycloalkyl and $R^2$ is hydrogen.

5. The compound according to claim 1, wherein $R^1$ is $C_{7-9}$ aralkyl which may be substituted with $C_{1-4}$ alkoxy, $C_{1-4}$ alkanoyl, $C_{2-4}$ alkoxycarbonyl, hydroxy, amino, nitro, trifluoromethyl or $C_{1-4}$ alkanoylamido and $R^2$ is hydrogen.

6. The compound according to claim 1, which is 2-amino-5-propylaminomethylpyrrolo[2,3-d]pyrimidin-4-one.

7. The compound according to claim 1, which is 2-amino-5-cyclopentylaminomethylpyrrolo[2,3-d]pyrimidin-4-one.

8. The compound according to claim 1, which is 2-amino-5-benzylaminomethylpyrrolo[2,3-d]pyrimidin-4-one.

9. The compound according to claim 1, which is 2-amino-5-dibenzylaminomethylpyrrolo[2,3-d]pyrimidin-4-one.

10. The compound according to claim 1, which is 5-piperidinomethylpyrrolo[2,3-d]pyrimidin-4-one.

* * * * *